United States Patent [19]

Lemelson

[11] Patent Number: 4,900,303
[45] Date of Patent: Feb. 13, 1990

[54] DISPENSING CATHETER AND METHOD

[76] Inventor: Jerome H. Lemelson, 48 Parkside Dr., Princeton, N.J. 08540

[21] Appl. No.: 843,990

[22] Filed: Mar. 25, 1986

Related U.S. Application Data

[63] Continuation-in-part of Ser. No. 636,239, Jul. 31, 1984, Pat. No. 4,578,061, which is a continuation of Ser. No. 201,531, Oct. 28, 1980, Pat. No. 4,588,395, which is a continuation-in-part of Ser. No. 885,263, Mar. 10, 1978, abandoned.

[51] Int. Cl.$^4$ .............................................. A61M 5/00
[52] U.S. Cl. ....................................... 604/54; 604/57; 604/285; 604/11; 606/213
[58] Field of Search ............... 128/334 R; 604/57, 59, 604/60, 54, 285–287, 890, 11

[56] References Cited

U.S. PATENT DOCUMENTS

| 3,221,745 | 12/1965 | Coover et al. | 128/334 R |
| 3,500,819 | 3/1970 | Silverman | 128/1.2 |
| 3,882,858 | 5/1975 | Klemm | 128/334 R X |
| 4,250,163 | 2/1981 | Nagai et al. | 604/890 X |
| 4,292,299 | 9/1981 | Suzuki et al. | 604/890 X |
| 4,307,075 | 12/1981 | Martin | 604/54 |

FOREIGN PATENT DOCUMENTS

| 215350 | 10/1909 | Fed. Rep. of Germany | 604/96 |
| WO85/02092 | 5/1985 | World Int. Prop. O. | '604/890 |

Primary Examiner—Dalton L. Truluck

[57] ABSTRACT

Medical catheters and methods are provided for dispensing and implanting materials and devices within the bodies of living beings. In one form, an implantable device or material is disposed within the operating head of a catheter which is caused to move through a body duct to a select location therein which location is detected either by externally scanning the body duct with radiation or ultrasonic energy or by viewing an image of the body duct adjacent the head of the catheter by means of a fiber optical viewing system including a fiber optic cable extending along the catheter. When properly located, a mechanical, electro-mechanical and/or fluidically operated mechanism in the head of the catheter is operated causing a select quantity of an implantable material or an implant to be forced from the head and caused to engage a select portion of the wall of the body duct and attach thereto to retain such implant or material in engagement therewith. In a particular form, attachment is effected by means of a biodegradeable adhesive which sets in situ per se or between the implant of implantable material and the tissue of the wall of the body duct. Thereafter the catheter is retracted and either completely removed from the wall of the body duct or is disposed at a second location and the procedure repeated with respect to a second implant or second quantity of material to be attached to the wall of the body duct.

10 Claims, 4 Drawing Sheets

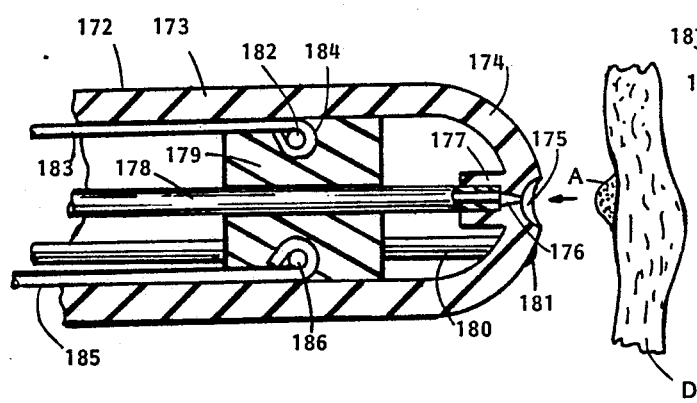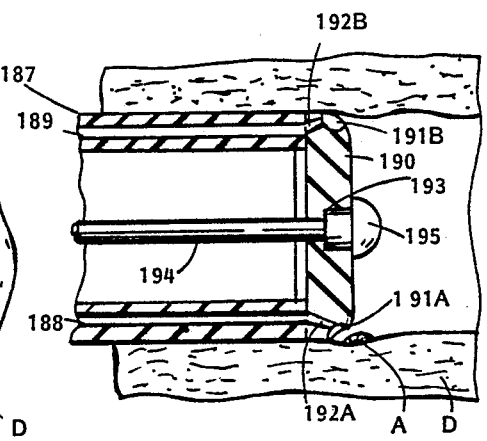
FIG. 17
FIG. 18

DISPENSING CATHETER AND METHOD

CROSS REFERENCE TO RELATED APPLICATIONS

This is a continuation-in-part of application Ser. No. 636,239 filed July 31, 1984, now U.S. Pat. No. 4,578,061, which was a continuation of Ser No. 201,531 filed Oct. 28, 1980 now U.S. Pat. No. 4,588,395 which was a continuation-in-part of Ser. No. 885,263 filed Mar. 10, 1978 now abandoned.

SUMMARY OF THE INVENTION

This invention relates to medical catheters and instruments employed to dispose or implant various materials for medicinal, treatment and repair purposes within a living being, such as against a select portion or the surface of a body duct or organ by ejecting or flowing same from the head of the instrument or catheter. The material is selectively dispensed by working and positioning the operating head of the catheter in alignment with a selected portion of a body duct or organ, by inserting the catheter a select degree into a body duct or by observing an image of the body duct by either fiber optic viewing means employing an eyepiece and light transmitted to and from the head of the catheter and/or by viewing a direct or reconstructed image on a video display formed by means of penetrating radiation passing through the body, which image shows the duct and operating head. Once the catheter head is so located, the material to be dispensed against the select location of the body duct is applied from the head by one or more of a number of means such as longitudinally movable piston, a pivoted piston, a swabbing, wiping or spray applicator moved along or through the head of the catheter such as by operating a pushpull shaft from the end of the catheter located exterior of the body or by means of a solenoid or motor located in or adjacent to the operating head. In a preferred form, medication, gauze or cellular material is adhesively bonded to the select tissue with a biodegradable adhesive and is retained thereagainst until both the adhesive and applied material biologically degrade in the presence of body fluid, for a period of time after the catheter is removed.

Accordingly it is a primary object of this invention to provide a new and improved apparatus and method for applying materials, medication and devices to select locations within the body of a living being for the purposes of beneficially treating, healing, repairing and arresting the flow of blood from tissue and wounds existing within the body of a living being.

Another object is to provide is to provide an apparatus and method for delivering a drug to a select site within the body of a living being and retaining same at such select site while slowing dispensing same to the tissue at such select site.

Another object is to provide a method for delivering and bonding a drug composition to a select portion of the wall of a body duct within a living being which method includes slowing releasing one or more drugs from such composition to beneficially affect tissue adjacent to the bonded composition.

Another object is to provide an apparatus and method for applying a dressing to a wound withing the body of a living being without the need to operate on skin and tissue.

Another object is to provide an apparatus and method for spreading or swabbing a medication against a select portion of the wall of a body duct of a living being.

Another object is to provide an apparatus and method for spray applying a liquid medication to a select portion of the wall of a body duct of a living being.

Another object is to provide improved composition of matter for applying medications and the like selectively within the body of a living being.

Another object is to provide improved adhesive compositions containing medications to be released therefrom within the body of a living being.

Another object is to provide a drug delivery system employing a self setting bio-adhesive composition containing medication which is slowly release therefrom as the set adhesive degrades within the body of a living being.

Another object is to provide improvements in medical devices, including drug applicators and dressing for use in the body of a living being and devices and systems for properly applying same to treat internal disease, wounds and other maladies.

With the above and such other objects in view as may hereinafter more fully appear from studying the specification, drawings and claims hereof, the invention consists of the novel constructions, combinations and arrangements of parts, but it is to be understood that changes and modifications may be resorted to without departing from the spirit and nature of the invention as claimed.

DESCRIPTION OF THE DRAWINGS

FIG. 17 is a side view with parts broken away for clarity of a portion of a catheter including the operating end thereof, showing means for manipulating said operating end by controllably deflecting or bending same in a select direction, and FIG. 18 is a side view with parts broken away for clarity of the operating end of an improved dispensing catheter.

In FIG. 1 is shown a first form of the invention comprising an assembly 10 formed of an elongated flexible hollow tube 31 made of a flexible plastic such as an elastomeric polymer or rubber and connected at one of its ends to an actuating device 11 which may be manually operated for urging the longitudinal movement of a flexible shaft 30 in the flexible tube 31, the combination defining what will be referred to hereafter as an ejection catheter. Depression of an actuator head or push button 20 by the movement of the human thumb thereagainst while a flange 12 forming part of the actuating device 11 is held by the fingers of the hand, urges shaft 30 longitudinally through the tube 31. The other end of tube 31 is inserted into a bore or opening 35 in a head or fitting 32 located at the end of the catheter, which fitting is an elongated bead-like hollow housing not much greater in diameter than the tube 31 and serving as a retainer and guide for a device or quantity of solid material to be implanted into the tissue adjacent said head when the latter is disposed at a given location in a body duct, such as an artery, the intestine, throat or other body duct. Fitting 32 has a tapered forward end 33 and a chamber defined by a cavity 34 of constant diameter extending from the end 33 thereof, into which chamber a piston 36 is slidably movable and is connected to the end of flexible shaft 30. Material, such as a medication in the form of a pill or solid cylinder 37, a viscous fluid such as a cream or salve, or a container for medication, is disposed within the chamber or cavity 34 in such a manner that it is normally retained therein but will be ejected from the end of the fitting when the piston 36 is urged forwardly by the forward movement of shaft 30. The material or pill 37 may be frictionally, adhesively or otherwise retained in chamber 34 so as to hold it therein until it is urged out of the operating end of head 32.

Figure 1:
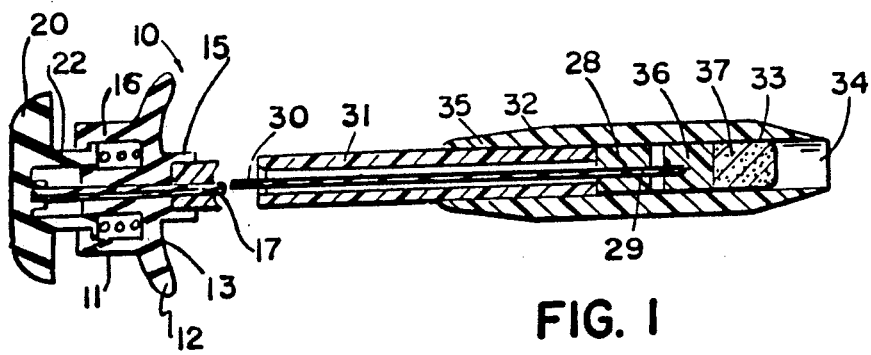
FIG. 1 is a side view in cross section of both ends of an elongated medical catheter having means for carrying and ejecting a solid material from its operating head or end.

The actuating device 11 comprises a hollow tubular body 16 connected to the finger grip 13, through which body the flexible shaft 17 extends to the tubular retaining means 22 of the pushbutton head 20. When head 20 is pushed forwardly by a force applied by thumb thereagainst while fingers hold the grip 13, the push-pull shaft 30 is urged forwardly through the flexible tube 31 and the piston 36, which is connected to the end of said shaft, is thereby urged forwardly in the cavity or chamber 34 so as to force the device or medication 37 which is disposed against or forwardly of the piston, out of the end of the fitting 32 and preferably, although not necessarily, completely from the end of said fitting so as to dispose the device 37 adjacent to tissue which surrounds or is adjacent the head or fitting 32.

The end of flexible tube 31 is adhesively bonded or welded to the tapered rear end 35 of the head end or fitting 32 of the catheter and is shown abutting a cylindrical plug 28 containing a passageway 29 extending axially therethrough which serves as a lineal bearing in which the flexible shaft 30 may be longitudinally driven forwardly, and rearwardly to urge the piston 36 to which it is connected, both forwardly and rearwardly. A helical spring is shown disposed beneath the head 20 and a retaining wall portion 12 of the actuating assembly for normally urging the head 20 outwardly from the actuating end and to maintain the piston 36 retracted prior to the ejection of the material 37 from the end of the head 32.

It is noted that a thin plastic film, wax or other material may be disposed across the opening in the cavity 34 of the head portion 32 of the catheter to maintain body fluids out of the passageway 34 until the wax or plastic film has been removed or ruptured by the forward movement of the solid material 37 as urged by piston 36 thereagainst. It is also noted that the finger operated actuating device 11 may be replaced by a piston grip mechanism containing a trigger which is finger operated and is used to urge the flexible shaft 30 longitudinally in the bore of the flexible cable or tube 31 for the purpose of ejecting the solid material or device 37 from the end of the head 32 or disposing at least a portion of 37 outwardly from the end of the head to engage or otherwise affect tissue within the human body adjacent the head.

Figure 2:
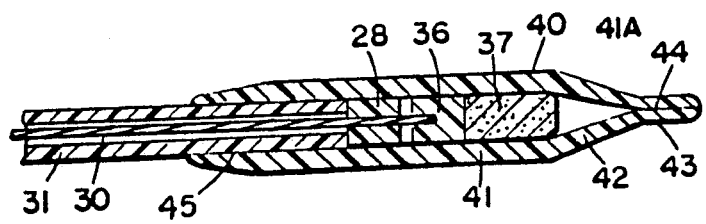
FIG. 2 is a side view in cross section of a modified form of the head end of a catheter of the type shown in FIG. 1 wherein such head contains a flexible wall portion which is normally closed or collapsed into a flat shape and may be opened by forcing a solid material or piston therethrough which material may be ejected from the open end of the expanded portion of the head.
Figure 3:
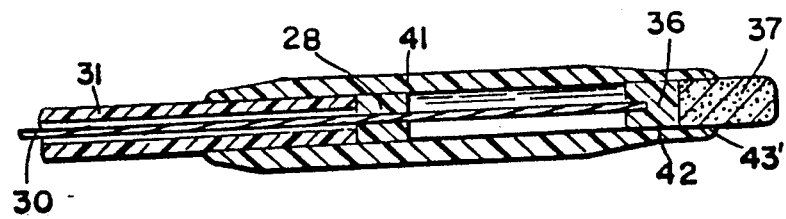
FIG. 3 is a side view in cross section of the device of FIG. 2 showing the solid material thereof being ejected from the end of the catheter.

In a second embodiment illustrated in FIGS. 2 and 3, the head end or fitting 40 of a catheter 39 has a tubular wall 41 having a tapered forward end 42, the end portion 43 of which is collapsed or formed closed, as illustrated, forming interface 44 which is normally in a sealing condition to close off the interior volume 41A until the tapered wall portion 42 is outwardly expanded so as to separate the interface 44 as illustrated in FIG. 3. When a piston 36 is urged forwardly by the forward movement of flexible shaft 30, it urges the solid cylindrical device or pill 37 through the tapered section 42 and the collapsed section 43 to either position it as illustrated in FIG. 3 protruding from the end of the end portion of the fitting 41 or to eject it completely therefrom so that it lies against the tissue adjacent the end of the catheter. Solid pill 37 may comprise or contain a drug for treattissue or may contain a radioactive element and may serve as a source of radiation located, when dispensed from the head of the catheter as described, immediately adjacent a tumor or malignancy for treatsame with such radiation. As provided in FIG. 1, the flexible pushpull shaft 30 is moved longitudinally in a flexible tube which is sealed within the rear portion of the bore of fitting 40 against the rear face of a thrust bearing or plug 28 and secured at its end to the piston 36 as described above. When the piston 36 is retracted to the position illustrated in FIG. 2, the memory of the plastic causes the outwardly expanded end 42 of the fitting 40 to collapse and assume the condition illustrated in FIG. 2 after which the catheter may be removed from the cavity or artery, sterilized and have a new device or plug of material 37 inserted therein for its next use.

The embodiment of FIGS. 2 and 3 as well as that of FIG. 1 may also contain one or more light pipes or fiber optic bundles extending along or within the flexible shaft 30 and through the pistons 36 to serve one or both of two functions, as conductors and receivers of light for observation or sensing the condition of tissue adjacent the end of the piston when projected from the end of the catheter head and/or as a conductor of light such as laser light which may be employed to perform surgery by vaporizing, cutting, burning or cauterizing tissue or bone disposed adjacent to or in contact with the projected and exposed end of the piston. Light from an external souce such as a laser may be piped through one light pipe or bundle and directed from the end of the piston which may comprise a lens for directing or focusing such light and reflections thereof from tissue or bone may be received by such lens or the end of the other light pipe and passed back along the cather for use in observing the tissue or bone by conventional means.

Figure 4:
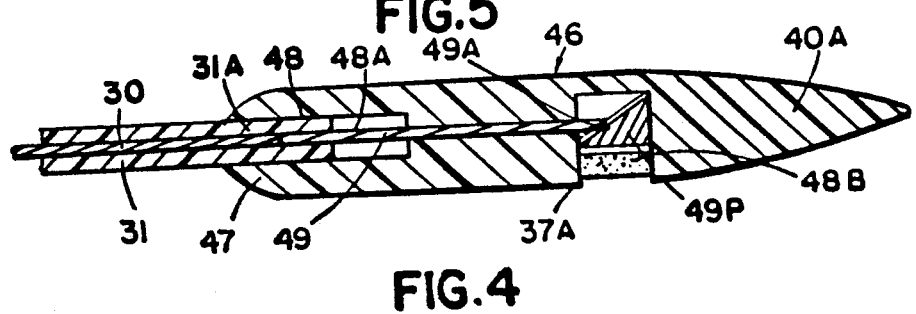
FIG. 4 is a side view in cross section of a modified form of the invention of FIG. 1 wherein a solid material is ejected from the side of the head of the catheter.

In FIG. 4, details are shown of a medical catheter assembly having a head or end fitting 46 with a tapered front end 40A and a rear portion 47 containing a cylindrical bore or cavity 48 extending therein from the rear end and in which the end 31A of a flexible catheter tube 31 is inserted and adhesively sealed or secured by heat sealing to the wall of the head 46. Longitudinally extending the passageway in the flexible tube 31 is a flexible push-pull shaft 30 which also extends through an extension 48A of the bore 48, in which it is slideably engaged, and from which extension the end of shaft 30 protrudes and engages the rear face of a piston 49P which is adapted to be urged by the forward motion of the shaft 30 longitudinally through a bore 49 which extends normal to the axis defined by the shaft 30 and bore 48. A plug or pill 48B is secured within the bore 49 beneath the outer surface of the head 46 and may be urged by the lateral movement of the piston 49P, outwardly from said bore to be ejected against tissue disposed adjacent the head 46 for the purposes described above. In other words, the end of flexible shaft 30, or an extension thereof, slideably engages or engages in a cavity in the tapered rear face of the piston 49P and when the shaft 30 is urged against the rear face of the piston 49P, it causes the piston to move laterally outwardly through the bore so as to eject the solid pill or material 48B therefrom.

Figure 5:
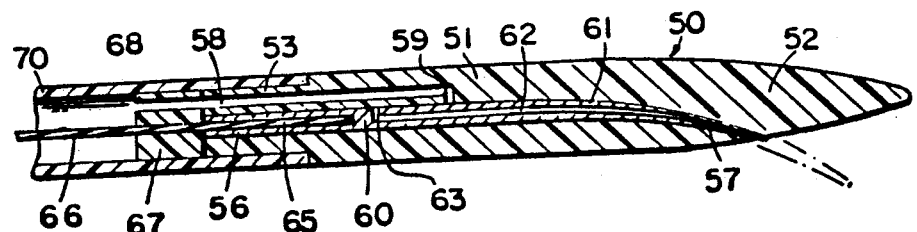
FIG. 5 is a side view in cross section of a modified form of the invention showing means for partially ejecting a hollow needle from the end of the catheter to cause it to be inserted into and through tissue located adjacent the end of the catheter.

In FIG. 5 is shown another form of the invention comprising a catheter having a head assembly 50 at one end thereof which includes a fitting or housing 51 having a tapered forward end 52 as shown and a rear end portion 53 of reduced diameter for frictionally retaining the end of a flexible plastic tube 70 thereagainst. Means are provided at the other end of flexible catheter tube 70 for applying fluid under pressure to the passageway 65 defined by the flexible tube 70 and then to a passageway 58 in the head 51 which latter passageway extends to the surface of a curved needle 60 having a curved head end 61 and a radial bore 63 extending to the interior passageway 62 of the needle 61.

The bore 56 through which the needle 61 extends, has a curved forward end portion 57 which is adapted to receive the curved forward end 61 of the needle 60 and to permit same to be urged therethrough beyond the side of the tapered side wall portion 52 of the head 51 of the catheter. If the needle 61 is formed of a spring-like material, such as a small diameter stainless steel needle, it may be arcuately deformed in the passageway 56 to permit it to conform to the curved forward section 57 thereof and to be partially ejected from the tapered end portion 52 of the head 51 so as to permit a fluid, such as a medication liquid, introduced into the interior volume of the tube 70, to flow through passageway 58 and then through a radially extension 59 thereof to an opening 63 in the side wall of the needle 61 whereafter the fluid may be flowed through the longitudinal opening 62 in the needle 61 and out the end thereof when the latter is suitably positioned within tissue immediately adjacent the cavity into which the head end 51 of the catheter has been inserted. While the tapered housing 51 of head 50 may be formed of metal such as stainless steel or rigid plastic, it may also be formed of a flexible plastic such as polyurethane resin permitting it to deform somewhat when the needle 61 moves therethrough.

In the embodiment illustrated in FIG. 5, a device, such as that illustrated in FIG. 1 or a pistol grip device is used to finger operate the flexible shaft 66 causing it to engage the end of the needle 61 causing the latter to be partially ejected from the end portion 52 of the head 51 of the catheter. After such location of the needle 61 has been effected, a fluid under pressure may be pumped through the passageway or interior 71 of the flexible catheter tubing 70 and flowed, as illustrated, to the hollow passageway extending through the needle 61 and out the end of said needle for its intended purpose.

While each of the embodiments illustrated in FIGS. 1-5 employs a flexible push-pull shaft 30 extending through the flexible catheter tube 31 for lineally actuating a piston to expell a capsule, quantity of fluent medication or other matter from the end of the catheter head, it is noted that the piston 28 of FIGS. 1-3 or 49F of FIG. 4 may be actuated by fluid pressure applied to the interior of the flexible catheter tube from the other end of the catheter such as by means of a manually operated piston moving a liquid in the tube, pump operation or valve opening to release fluid pressure to the tube. The pistons 36 and 49P may also be moved as described to expell material from the catheter head by means of a miniature motor or solenoid mounted in the head of the catheter and controlled in its operation by means of wires conducting electrical energy along the catheter to the head from a source of such energy such as a battery located exterior of the catheter at ther other end thereof and controlled by means of a manually operated switch forming part of the assembly at the other end.

It is also noted that the shaft 30 may also be rotated in the catheter to effect movement of the piston for expelling the material from the head by means of a suitable helical screw advancing the piston in the head when rotated by the rotating shaft to slowly expell the material from the head and/or advance the needle 61 from the head.

The advancing and/or retracting means for the catheter piston or needle described above may also be vibrating electrical transducer such as a piezoelectric crystal or solenoid operating when vibrated by electrical energy conducted thereto through wires extending through the catheter tube, a simple lineal travelling mechanism such as an inchworm motor mechanism for advancing the piston through the catheter head. A bimetallic element mounted in the catheter head may also be employed to advnce the piston when the bimetallic element is heated and deflected by electrical resistance heating provided by electrical energy fed to a resistance heater in the heat through wires extending along the inside of the catheter tube from a source of such energy connected to the wires at the other end of the tube.

In yet another from of the invention, the piston in the head of the catheter or a similarly functioning device operable to expel a capsule or quantity of matter from the head as described, may be retained against a compressed spring, such as a coil spring located in the head of the catheter and may be release from such retained position to be forced by the spring along the bore in the head in which it is seated to expell the capsule or matter from the head as described when a miniature latch or retainer is released by fluid pressure applied along the catheter tube or by pushing or rotating the flexible shaft extending along the tube to the head, from the other end of the catheter.

It is further noted that the arrangement illustrated in FIG. 5 wherein a needle is projected from the catheter head to inject fluid into tissue adjacent the head, may be employed to effect surgery with respect to tissue adjacent the head by heating and/or cooling the needle or a modified form thereof before and/or after it is extended from the catheter head. Heating may be effected by resistance heating means located in the head and energized by electrical energy conducted to the heat through wires extending from the other end of the catheter and cooling by means of liquid nitrogen or other cryogenic liquid at low temperature which is pumped or pressure forced along the catheter tube from the other end thereof after the needle or otherwise shaped implement is projected from the head of the catheter adjacent tissue or bone to be so operated on.

In yet another form of the invention, laser light at sufficient intensity to corterize or otherwise heat tissue or a surgical blade or tool may be generated and directed along one or more light pipes or fiber optical bundles extending through the center of the catheter tube and either applied directly to tissue adjacent the head through a lens or optical devices which is located at the end of the head fixed or movable therefrom as desriibed to permit the light energy to be properly directed into or toward tissue adjacent the head. If the fitting is a needle which is a light pipe or conductor, it may be inserted into tissue adjacent the head when it is moved from the head as described and may thereafter conduct intense light energy into the tissue into which it is inserted. The needle 61 of FIG. 5, for example, may comprise a solid or hollow needle-like member made of light conducting glass or ceramic material with the tapered end thereof adapted to penetrate tissue when it is projected from the head 51 as described. The flexible actuating cable 66 may comprise a glass or plastic filament or a bundle of such filaments clad with higher refractive index material to define a light conductor for laser light energy directed from a laser into the end thereof which is exterior of the body into which the catheter is inserted wherein the laser light is operable to heat the tip or end of the needle or a metal fitting secured thereto for surgical purposes with respect to tissue into which the end of the needle is inserted as described. The laser light energy may also be directed from the end of the needle into tissue into which the needle is inserted and penetrates. A flexible multiple strand metal wire combined with one or more light pipes or fiber optical bundles extending along the core of the wire, parallel thereto exterior thereof or spirally wound around said core may also be employed to conduct laser light energy to the needle or surgical tool 61 when it is projected from the head 51 of the catheter to heat the end of the needle or a metal fitting secured thereto to a temperature whereby it may be used to cauterize, burn or otherwise affect tissue into which it is inserted or against which it is disposed.

The head 51 of the catheter or the end thereof may also serve as a cauterizing or surgical tool when heated to a temperature whereby it will burn or corterize tissue by laser light energy directed thereagainst from a light pipe or pipes defined by the wire 66 or secured thereto as described above and extending to the rear end of the head or a passageway through the head to near the end thereof to be heated. The end of the head 51 may be shaped as shown in FIG. 5 and may comprise a fitting such as one made of stainless steel or a noble metal such as platenum which will resist corrosion from the high temperature to which it is so heated.

The catheter shown in FIGS. 1-3 may also be modified with all or part of the front portion of the piston 36 or a modified form thereof adapted to be projected from the end of the head in which it is retained while the head is inserted into the body cavity and adapted thereafter to be heated as described above by an electrical resistence heating element disposed therein or laser light energy conducted thereto through a light pipe or pipes connected or coupled to the piston and defining or supported by the actuating cable 30. The piston 36 may comprise a blade, a needle or a plurality of needles made of metal, ceramic or glass and heated as described for corterizing or performing surgical operations with respect to tissue against which or into which it is inserted when the head of the catheter is predeterminately located within the human body. The piston 36 may also comprise or contain a lens or a number of lenses which are optically connected or coupled to the end or ends of the light pipe(s) for viewing tissue adjacent the head by directing viewing light from the other end of the catheter along one light pipe or bundle through the lens to tissue and directing the reflected light back up along another light pipe or bundle to a viewing eyepiece or photoelectric cell or other form of electro-optical monitor such as a video camera. In a similar manner, the piston 49P of FIG. 4 may be similarly heated and constructed as described above for performing surgery and/or cauterization with respect to tissue at the side of the head 46 when laterally projected therefrom as described. Piston 49P may also comprise a blade or otherwise shaped tool or any optical element such as a lens, prism or missor for two way communication as described above with respect to viewing tissue adjacent the side of the head by means of light pipes extending along or within the cable 30, employed to actuate the piston, from a source of light energy and a monitoring device at the other end of the cable.

A catheter employing cryogenics and heating by means of laser light energy or resistance heating means as described may also be employed for combined hot and cold surgery or corterization. For example, after the head or piston or needle is heated as described and employed for surgery, a cryogenic liquid such as liquid nitrogen may be pumped to the head through a passageway in the tubular jacket 31 or 70 to the end thereof and through the head and/or needle or piston and circulated, if necessary by return flow through another passageway in the jacket to perform cryogenic surgery or corterization or to cool the head or tool immediately after it is so heated.

In a modified form of the embodiment of FIG. 5, needle 61 may be replaced with a straight needle which is longitudinally movable in a lineal passageway extending at an angle to the longitudinal axis of the head and opening at the side of the head at the point shown and actuated to move from the opening by the flexible shaft illustrated.

Figure 6:
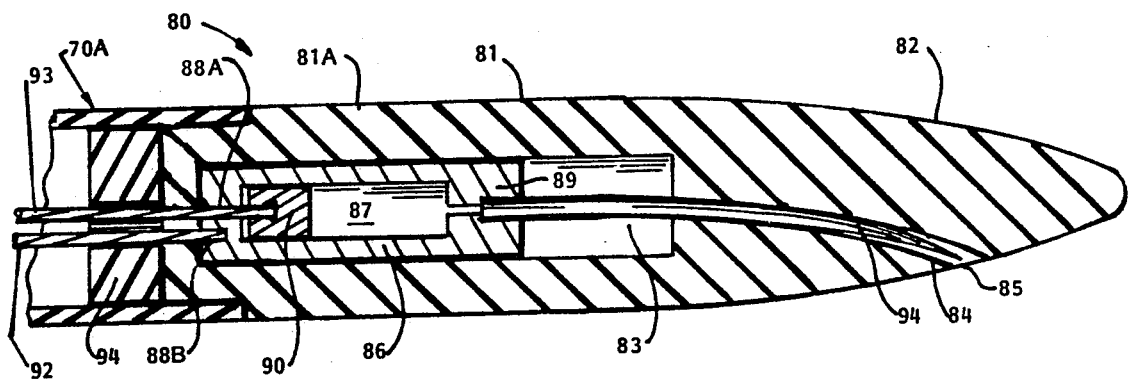
FIG. 6 is a side view in cross-section of a modified form of the catheter shown in FIG. 5.

In FIG. 6 is shown a modified form of injection catheter of the type shown in FIG. 4. The catheter 80 includes an operating head 81 with a smooth tapered end 82 extending from a constant diameter rear portion 81A having a reduced diameter rear portion 83 which is frictionally gripped by and secured to the front end portion of a flexible catheter tube 70A which is a modified form of tube 70 of FIG. 4 in that it accomodates two flexible shafts therein, denoted 92 and 93 which extend the length of such tube 70A from respective manually operated actuating means of the type described wherein both such shafts may be simultaneously urged to move toward the catheter head by hand and one of such shafts, 93, which is operable to effect injection fluid pressurization and flow, may be separately actuated from the other shaft. A constant diameter bore 83 in the rear of the head 80 extends partly through the head and slidably supports a first piston 86 which piston contains a second piston 90 slidable in a bore 87 extending partly through such first piston. A second bore 84 of lesser diameter than bore 83 extends forwardly of bore 83 and curves toward one side of the tapered end 82 of the head to an opening 85. Disposed within the curved passageway 84 is an arcuately shaped hypodermic needle 94 which is secured at its rear end portion within an extension of bore 86 and has its passageway communicating with the remaining volume defined by bore 86 so that liquid medication disposed within the bore 86 may flow into and through the needle to be ejected from the end thereof.

During the movement of the catheter head to a select location in a body duct the needle 94 is retracted as shown in FIG. 6 with its sharp end disposed inward of the opening 88 so that it will not interfer with the forward movement of the catheter to an operating location in the body. When the head 81 is at an operative location within a body duct such as a vein or artery, needle 94 may be caused to move forward through curved bore 84 to project its sharp end outwardly from the sidewall of head 81 so as to penetrate tissue of the body duct in which the head 81 is disposed and/or an organ or other object aligned therewith.

The rear wall 88 of the hollow piston 86 is provided with a central passageway 88A extending therethrough, in which passageway flexible push-pull shaft 93 is slidably movable to permit it to move the sub-piston 90 longitudinally through the bore 87 to force liquid medication therein through the needle 94 when the latter is projected from the opening 85 by the forward movement of piston 86. Such forward movement is effected by urging flexible shaft 92 forward from the outer end of the catheter as the end of shaft 92 is secured within a cavity in the endwall 88 of piston 86. A cylindrical plug or disc 94 is secured within the catheter tube or jacket 70B behind the read end wall 81B of the head and contains two passageways or bores extending therethrough for slidably supporting the end portions of the shafts 92 and 93.

During the movement of the catheter through a body duct to position the head 81 at a select location therein prior to projecting the hypodermic needle from the head, piston 86 is disposed retracted in bore 83 while sub-piston 90 is disposed retracted within the interior bore 87 of piston 86 as shown. A select quantity of liquid medication to be injected into tissue or the body duct from the needle is disposed in the volume between the end of the passageway 83 and the endwall 89 of piston 86. When head 81 is properly located, shafts 92 and 93 are urged forward together to selectively project the sharp end of needle 94 beyond opening 85 without flowing liquid therefrom and, upon effecting the desired degree of needle projection, piston 90 is moved forward through passageway 87 by urging shaft 93 forwardly causing part or all of the liquid in volume 87 to be forced through the needle. Adhesives or solvents may be applied to bond the end of sheaving 70A to the rear end of head 81, the shaft 92 to the rear wall 81b of piston 86, shaft 93 to subpiston 90 and the read end of needle 94 to the front wall 89 of piston 86. Such components as the head 81 and piston 86 may molded of multiple plastic components welded or bonded together.

Figure 7:
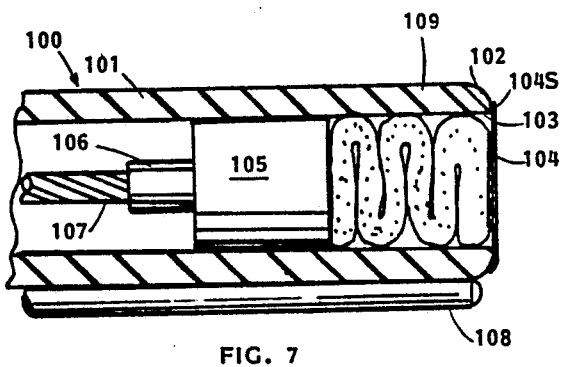
FIG. 7 is a side view with parts broken away and sectioned of the operating end of a dispensing catheter or instrument operable for disposing a length of a strip of dressing against a select portof a body duct or organ of a living being.

In FIG. 7 is shown details of a portion of a medical instrument 100, such as the operating head of a catheter, which is utilized to dispense a quantity of a flexible material, such as a strip of porous plastic, tissue, gauze or the like or a combination of such materials. In FIG. 7, the material dispensed is in the form of an elongated strip 109 of cellular or porous material which is folded a number of times on itself. The instrument 100 has a cylindrical side wall 101, the front end 102 of which is rounded or tapered and has an opening 103 therein extending to the interior of the catheter or instrument head. Disposed across such opening and sealed by welding, heat sealing or adhesive means is a thin disc 104 of plastic film or the like which serves to cover the opening while the instrument is inserted into a body cavity and worked or moved to a select location therein. Engaging the rear end of the folded material 109 is a piston 105 having a rearwardly extending tubular portion 106 which contains and is fastened to a flexible push-pull shaft 107 extending through the catheter from the other end thereof and manipulatable by hand or motor means to drive the piston forward to force the material 109 through the open end 103 thereof by unbounding or tearing the circumscribing seal 104S between the rim of the opening and the disc-shaped cover 104. Notation 110 refers to a tacky adhesive, such as biodegradable bio-adhesive, applied to the front end portion of the folded strip 109, which may be made to engage tissue adjacent the front end of the catheter when such strip is forced through and beyond the opening 103, as shown for example in FIG. 8. Notation 108 refers to a transmit-receive fiber-optic cable bonded or otherwise secured to the outside surface of the wall of the housing 101 and terminating near the end 102 thereof to permit light passed along one bundle of the cable 108 to be projected from the end 108A thereof and to permit such light to be reflected off tissue and directed back to the end of the cable 108 to be transmitted along a second bundle of optical fibers to a viewing eye-piece [not shown] at the other end of the cable.

Figure 8:
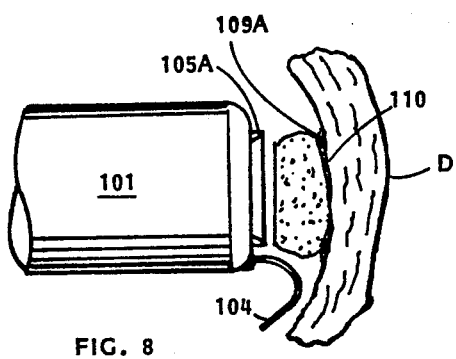
FIG. 8 is a side view of the device of FIG. 7 and a modified form of the medical material thereof, shown dispensed and adhesively bonded to the wall of a body duct.

In FIG. 8, the forward end 105A of the piston 105 is shown extending beyond the end of the housing 101, having disposed a disc-shaped, flexible, porous or cellular pad 109A containing a tacky adhesive 110 coated on its front face, to be pressed and disposed against the inside surface of a body duct D, as shown, to permit such porous member to serve one or more purposes such as to retain and dispense a medication, stop internal bleeding, dispose a biological agent or agents against the wall of the body duct or to perform a plurality of such functions after it has been forced through the opening 103 and has caused the thin sheet disc 104 to be torn away from its sealing rim, as shown.

Figure 9:
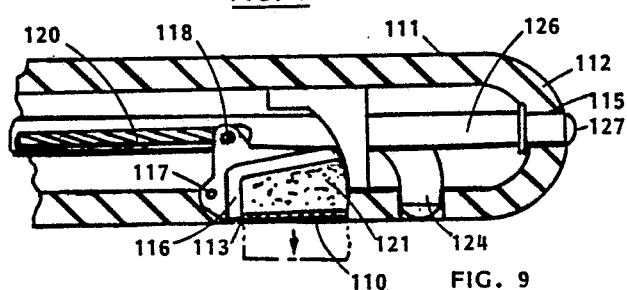
FIG. 9 is a side view with parts broken away and sectioned for clarity of the operating end of a catheter operable to dispose a material, such as a medication or dressing from the side or end wall thereof.

In FIG. 9 is shown a modified form of the apparatus of FIGS. 7 and 8 wherein a flexible, porous pad 121 which may comprise a retainer for a medication or biological agent, tissue or the like, is dispensed from the side wall of the catheter, preferably against the wall of a body duct in which the catheter is dispensed. As in FIGS. 7 and 8, a tacky adhesive 110 of the type described, is coated on the outer surface of the porous disc 121 and the opening 113 through which such disc is forced, is preferably covered with a thin disc-shaped plastic film or sheet which is heat sealed to the rim of the opening and which may be torn away from such seal, as in FIG. 8, by forcing the porous member there against utilizing a mechanism which consists of a retainer 116 which is pivotally fastened by means of a pin 117 extending through the wall 111 of the catheter head. A flexible push-pull shaft 120 extends along and through the catheter from the other end thereof and is pinned by means of a small shaft or pin 118 to an extension of the retainer 116, as illustrated. The push-pull shaft 120 thus serves as a means for urging the fitting 116 in pivotal movement about its pivot 117 to cause the fitting 116 to move and eject or force the outer face of the porous disc 121 against tissue, such as the wall of a duct aligned therewith.

In FIG. 9, notations 124 and 126 refer to fiber-optic cables having at least two pairs of fiber-optic bundles, one for carrying light from a remote source and the other for receiving reflections of such light and transmitting same to the other end of the catheter where such light may be utilized to generate a viewable image of the fluid and body duct immediately adjacent the operating head of a catheter and/or to modulate signals output by a photoelectric detector or detector array, which signals are computer processed and analyzed to automatically determine the characteristics of the image information adjacent the catheter head. A second fiber-optic cable 126 containing light transmitting and receiving means 127 at its ends, extends longitudinally through the catheter and terminates at an opening 115 in the end wall 112 of the catheter or head 111 for scanning the environment immediately adjacent the end of the catheter to permit a person at the other end of the catheter to further view or detect information relating to the condition of the wall of the body duct to be treated. It is noted that the side wall 111 of the operating head of the catheter may be specially shaped, not only with an opening 113 therein through which the flexible pad or plug 121 may be passed to bring it into contact with the inside surface of the wall of the body duct but also be shpaed to receive and retain the pin 117 which pivotally supports the fixture 116 containing the material 121 to be dispensed, within the head of the catheter.

The fixture 116 is illustrated as an L-shaped retainer, although it may be in the form of an open cup-shaped container, which is operable to slidably pivot through the opening 113 in the side wall of the catheter to dispose the porous material 121 outwardly from the side wall. Such fixture 116 may also be located to pass the material through an opening in the end wall 112 of the head of the catheter so as to pivot outwardly and laterally therefrom to dispose the flexible material 121 against the inside surface of the side wall of the body duct and out of the way of the side wall of the catheter so as to prevent its removal or movement from the location of the catheter wall against which it is disposed when the catheter is removed from the body duct. In a modified form, the end wall 112 of the catheter may itself be pivotted on the side wall and may contain an indentation therein, in which indentation material, such as the plug or pad 121, is contained and may be disposed against a select portion of the side wall of the body duct in which the catheter is located, by pivotting such end wall utilizing a flexible push-pull shaft 120, as described. A further mechanism operated by the push-pull shaft pivotting such end wall, may be used to eject the material 121 from the cavity in the pivotted end wall portion of the catheter head so as to force it against the select portion of the side wall of the body duct, after which the push-pull shaft is retracted causing the pivotted end wall portion of the catheter head to retract leaving the material 121 in place against the body duct wall and permitting the catheter head to be removed from the body duct without interfering with the deposited material.

If an adhesive coating is applied to the outside surface of the medication or porous material 121, as in FIGS. 7 and 8, and is allowed to set in situ against the wall of the body duct, the flexible material 121 will remain against the body duct while the fixture 116 is pivotally retracted into the opening 113, permitting the catheter to be slidably removed from the body duct without removing the material 121. However, if such material is pivotally disposed against the wall of the body duct from the end of the catheter head, as described above, and is located beyond the end of the catheter head by means of a fixture of pivotting portion of the end wall of the body duct, there will be no interference between the moving catheter head and the dispensed material.

The cellular or porous materials 109 and 109A of FIGS. 7 and 8, as well as those described hereafter, may be formed of a variety of flexible or rigid open or closed cell organic or inorganic biodegradeable resins containing one or more of a variety of medications impregnating or coating same and adapted to be slowly dispensed therefrom to the body duct and/or tissue to which the porous material is adhesively bonded as such adhesive and porous material degrades or dissolves under the action of body fluid. A mixture of one or more medications per se or in microcapsule containers mixed with a biodegradeable organic or inorganic adhesive may also be coated on or impregnated throughout the cellular material to be disposed as described from the instrument or catheter head. Such an adhesive-medication mixture or adhesive-biodegradeable-capsule medication mixture may also be dispensed per se against or into a select portion of body duct tissue by the catheters illustrated particularly those of FIGS. 5, 6, 12, 14, 15 and 16.

Figure 10:
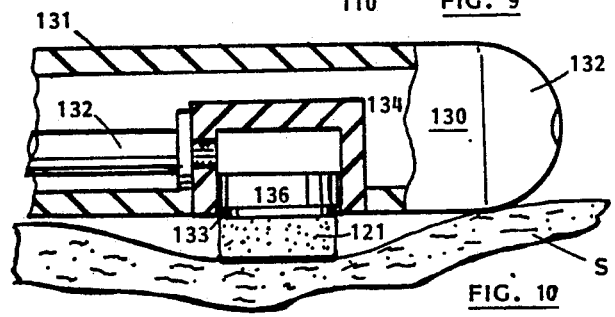
FIG. 10 is a side view with parts broken away and sectioned of a modified form of the catheter of FIG. 9.

In FIG. 10 is shown a modified form of the apparatus of FIG. 9 including an instrument or catheter assembly 130 having a tubular side wall 131 and an end wall 132.

Disposed across an opening 133 near the end of the side wall is a disc-shaped plug of medication or flexible porous material 121 containing a medication, of the type described, which is urged to move through the opening 133, as illustrated, against the surface of the body duct wall by means of a piston 136 which is slidably movable in a cylinder 134 attached to or forming part of the side wall 131 and sealed to the periphery of the opening 133. Fluid pressure for forcing the piston radially through the cylinder to locate the medication or porous material 121 as illustrated, is applied through a flexible tube or hose 135 connected to the side wall of the cylinder 134 across an opening therein and connected at its other end through a valve to a source of fluid pressure, such as air pressure, which may be applied to move the piston. Negative pressure applied to line 135 may be utilized to retract the piston after the material 121 has been adhesively bonded to the surface of the body duct S, as illustrated.

Figure 11:
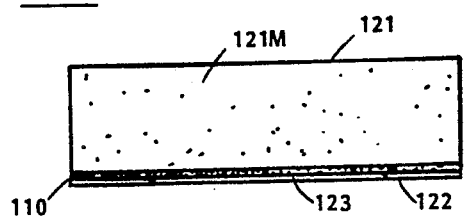
FIG. 11 is a side view of a porous dressing and/or drug dispensing material of the type dispensed by the devices described.

In FIG. 11 is shown details of the porous material 121 which may also be applied to the materials 109 and 109A of FIGS. 7 and 8. Such porous material 121 is formed of a cellular, preferably biodegradeable polymer or gauze formed of a biodegradeable material 121M and containing one or more medications to be dispensed therefrom, such as a blood coagulant, antibiotic, biological or chemical agent or agents useful in healing, tissue growth or in performing one or more other desireable functions. Bonded to an outer surface 121S of material 121 is a layer 110 of the described biodegradeable, self-setting, tacky adhesive. Disposed across such adhesive is a film 122 of biodegradeable material which degrades upon contact with body fluid permitting the adhesive to contact the surface of the body duct. Notation 123 refers to one or more openings in the film 122, which may also be a porous film, allowing the adhesive to be flowed therethrough when the pad or plug 121 is compressed and to engage and set against body tissue as described. If the adhesive 110 permeates all or the surface stratum of the cellular material 121, and is normally retained behind a cover or film such as 104 of FIG. 7, extending across the opening in the instrument or catheter head, the film 122 may be eliminated.

Figure 12:
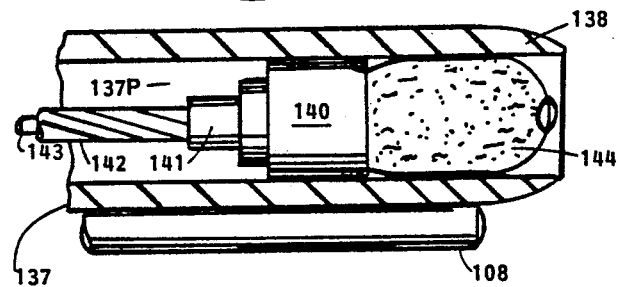
FIG. 12 is a side view with the side wall sectioned, of a catheter head operable to dispense or wipe a porous member at the end of the catheter against tissue adjacent the end thereof.

In FIG. 12 is shown a modified form of the apparatus of FIG. 7, comprising an instrument or catheter having a tubular, rigid or semi-flexible side wall 137, preferably of cylindrical shape, with a tapered end 138 and an opening 139 at the end thereof. Slidably disposed within the passageway 137P of the tubular side wall 137, is a piston 140 having a fitting or tubular extension 141 extending rearwardly thereof and connected to a multi-wire flexible push-pull shaft 142 containing a fiber-optic cable 143 extending longitudinally therethrough from the other end of the catheter. Such cable extends through the piston 140 and a cylindrical, cellular, porous medication containing member 144 which is normally retracted, as illustrated, and may be projected from the open end of the head or instrument by forward movement of the shaft 142 and piston 140 engaging the rear end of the material 144, to dispose same against tissue of the duct in which the instrument or catheter head is disposed. The apparatus illustrated in FIG. 12 may be used to perform a number of functions including the dabbing, wiping or swabbing of the material 144 against the select portion of the surface of body tissue for wipe-applying medication or other material it contains against such tissue by one or more longitudinal movements thereof outwardly from the end of the instrument. While notation 143 may comprise a fiber-optic cable utilized to transmit and/or receive light passed longitudinally from the end of the instrument to observe tissue adjacent thereto, it may also define or contain a small tube for supplying liquid medication to the porous member 144 while an auxiliary fiber-optic cable 108 of the type described in FIG. 7, is utilized for transmitting and/or receiving light energy for the purpose described.

Figure 13:
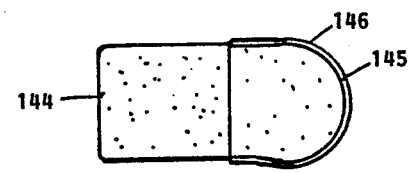
FIG. 13 is a side view of a material dispensable by the catheter of FIG. 12.

In FIG. 13 is shown a modified form of the porous member 144 containing a cup shaped cap or coating 146 disposed against the rounded end wall thereof and preferably made of a biodegradeable material which is either applied to a select portion of the surface of the body duct against which it is disposed or dissolved upon contact with body fluid permitting the end surface 145 of the cylindrical plug 144 to be disposed directly against the body duct wall.

Figure 14:
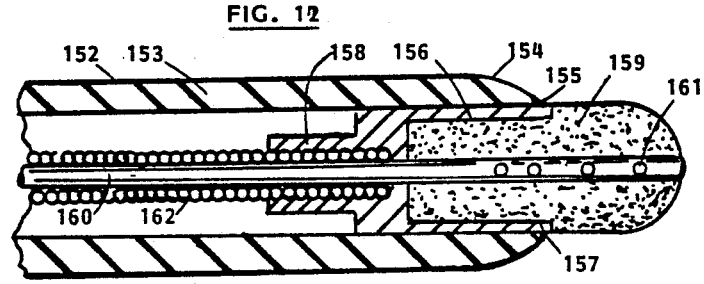
FIG. 14 is a side view with parts broken away for clarity of a modified form of the catheter of FIG. 12.

In FIG. 14 is shown a modified form of the apparatus of FIG. 12 comprising an instrument or catheter 152 having a cylindrical tubular side wall 153 and a rounded end wall 154 having an opening 155 therein through which opening a cylindrical, bullet-shaped, flexible, porous member 159 may be passed by the longitudinal movement of a piston 156 effected when a flexible, push-pull shaft is operated as described. The piston 156 contains a rearward tubular extension 157 in which a spirally wound single or multiple wire flexible hollow shaft assembly is secured, as shown. Extending longitudinally through the wire shaft 162 is a flexible tube 160 which extends completely through the piston and through a passageway in the porous member 159. A plurality of openings 161 in the side wall of the tube 160 permit liquid medication to be flowed through the tube 160 to the porous cells or interstices of the bullet shaped plug 159 to permit such medication to be dispensed by a wiping or swabbing action caused when the piston 156 moves the cellular plug 159 against a select portion of a body duct wall. Notation 158 refers to a hollow extension of the piston 156 for holding and retaining the rear portion of the cellular plug 159 which is preferably bonded in place therein. It is noted that one or more fiber-optic cables may also extend through the center of the tube 160 to provide illumination and/or operating laser light passing from the end of such tube to tissue and fluid within the body duct as well as a receiving fiber-optic bundle for viewing purposes as described.

Figure 15:
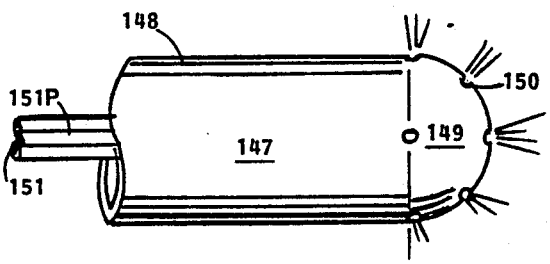
FIG. 15 is a partial side view of the operating end of a instrument or catheter operable to spray apply medication and/or repair material to select portions of a body duct.

In FIG. 15 is shown a modified form of the apparatus of FIG. 15, which includes an instrument or catheter 147 having a cylindrical tubular end or head 148 the end wall 149 of which is illustrated as being semi-spherical in shape and containing a plurality of openings 150 therein extending from one or more of respective flexible tubes 151 which extend from the other end of the instrument or catheter and are connected to one or more sources of fluid, such as liquid medications, to be dispensed by spraying or stream flowing through the openings 150 when the end of the catheter or instrument is disposed in alignment with a select portion of a body duct or organ. It it is desired to inject one or more streams of such liquid into the cells of the tissue of the wall of the body duct, sufficient pressure may be applied to one or more of the lines 151 to form one or more high velocity streams of such liquid medication which penetrates the tissue and are thus forced into the tissue cellular structure. It is also noted that such high velocity fluid stream may also be employed to perform an operation on tissue, such as rupturing or rendering porous cells of the surface stratum of the body duct wall for the purpose of administrating medication thereto dispensed from the instrument 147, as described, for cleaning, unclogging or otherwise affecting such tissue and/or deposits thereon. In other words, the instrument 147 may be utilized for cleaning or unclogging arteries, beneficially affecting intestinal tissue, applying medication or medications, thereto, or a combination of such functions.

It is also noted that one or more of the openings 150 in the end wall 149 of the operating head 148 of the instrument 147 may also be utilized to receive and pass laser light energy from one or more fiber-optic bundles or flexible light pipes 151P to tissue and/or deposited material immediately adjacent the end wall for cleaning, unclogging or beneficial operation purposes. Accordingly, one or more of the flexible tubes of the tubular array 151 may comprise fiber-optic cables for performing either or both the functions of operating on tissue and/or viewing tissue while one or more of the tubes 151 may be utilized to conduct liquid or gaseous material and pass same through one or more of the openings 150 in the end wall 149.

Figure 16:
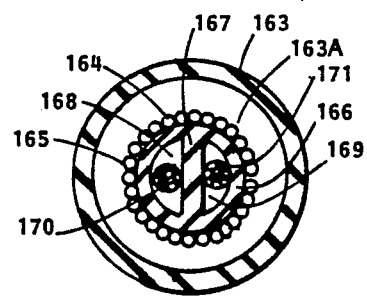
FIG. 16 is an end view in cross section of a catheter having multiple chambers for dispensing one or more fluids and fiber optic cables for viewing and or operating purposes.

In FIG. 16 is shown a modified form of instrument or catheter head formed of a cylindrical side wall 163 having three separate volumes contained therein through which different fluids may be flowed for the purposes described. A first annular volume 163A surrounds a flexible elongated assembly 164 extending the length of the catheter and comprising a helical array of wires 165 surrounding a cylindrical tubular extrusion 166 formed with a central spacer 167 extending the length thereof, and dividing the interior volume into separate volumes 168 and 169, each of which contains a respective fiber-optic cable 170 and 171. The fiber-optic cables may be utilized for viewing purposes as described, wherein one or both of such cables may also be utilized for conducting high intensity laser light energy along the instrument or catheter from a source exterior of the body and utilized, when projected from the end of the catheter, for operational purposes as described. The flexible shaft 165 may be utilized to move a member, such as the porous plug 159 of FIG. 15, through the opening in the end of the instrument or catheter head or may be utilized to permit a force to be applied to the catheter head in a manner to deflect or bend such head to permit its angle to be varied with respect to the body duct in which it is disposed to permit variable viewing and/or dispensing of material or direction of laser light therefrom.

In FIG. 17 is shown a modified form of the apparatus of FIGS. 14 to 16, comprising a catheter which may be operated to dispense a small quantity of an adhesive material per se or in combination with one or more chemical and/or biological materials against a select location within a body duct or organ for the purpose of performing one or more of the functions of repairing injured tissue, destroying diseased tissue,, beneficially treating dieseased tissue, destroying disease elements in tissue or in a body duct adjacent tissue or slowly releasing such material or materials to the body at a select location or site within the body. The drawing illustrates the operating end or head of a catheter 172 and a portion of the wall of a body duct D having a small quantity of an adhesive or adhesive mixture denoted A deposited against and bonded to a select portion of the surface of the duct by the tubular instrument or catheter 172 with the working end 174 of the latter retracted or withdrawn from engagement with the duct wall after the material A has bonded and/or partially set against the tissue of the duct.

The catheter end or head 172 is formed with a tubular wall 173 with a rounded or semi-spherical end wall 174 having a central cavity 175 formed in its outer surface into which cavity an adhesive or adhesive mixture is caused to flow, preferably after abutment of the end wall against a select portion of the surface of the body duct or organ D to close off the cavity and define the location of the glob of adhesive to be deposited. A select quantity of adhesive is then force flowed through a tapered passageway 176 in the end wall 174 behind the cavity which passageway extends from an elongated cavity in a rearwardly extending tubular formation 177 of the end wall. An elongated flexible tube 178 extends from the other end of the catheter and is sealed at its end within the passageway of the tubular formation 177. Pressuring the fluent adhesive in the tube 178 or a gas coupled thereto behind a quantity of such adhesive causes adhesive to flow through passageway 176 to cavity 175.

Also shown in FIG. 17 is a send-receive fiber optic cable 180 with a two way lens assembly 181 at its end exposed to the exterior of the end wall 174 for forward viewing the body duct from the other end of the catheter by conventional means as described. Means is also provided to controllably bending the end portion of the catheter to dispose, for example, the cavity 175 in alignment with or against a select portion of body duct wall tissue which may be located lateral to the head of the catheter when normally disposed in the body duct. Two flexible push-pull shafts 183 and 185 extend from the other end of the catheter and and may be selectively and controllably caused to respectively push and pull to apply a torque force to a plug or insert 179 secured within the catheter head or end to cause the flexible tubular wall 173 to bend or deflect in a select direction to dispose the end thereof at an angle to the longitudinal axis of the catheter head and/or the duct wall. Flexible push-pull shaft 183 is shown with its end 184 bent and looped abound a pin 182 supported at one side of the plug while the other shaft has its end similarly deformed and extending around a second pin 186 secured to the opposite side of the plug or insert 179. The flexible shafts 183 and 185 are supported for their longitudinal movement by one or more inserts located upstream of the catheter end portion shown, through which inserts such shafts extend to the other end of the catheter to provide sliding bearing support therefore.

In FIG. 18 is shown a modification of the embodiment of FIG. 17 which is operable to deposit and bond a plurality of portions of adhesive material at a select location or locations of a body duct wall. The catheter or instrument has a tubular wall 187 near its operating end, which wall contains a plurality of passageways, two of which 188 and 189 and shown and extend from the same or different sources of liquid or fluid adhesive and/or drug material to be dispensed. Sealed to the end of the tubular wall 187 is a disc shaped end wall 190 having a plurality of cavities, two of which are shown and denoted 191A and 191B, are formed in the rounded outer rime of wall 190 and communicate with the passageways 188 and 189 through respective tapered passageways 192A and 192B which extend to the rear surface of wall 190 aligned with the passageways 188 and 189. By controlling the fluid pressure applied to the passageways 188 and 189, select quantities of adhesive material may be made to fill selected or all of the cavities or adhesive material previously disposed in such cavities may be forced and dispensed therefrom. In other words, several techniques may be employed to operate the apparatus of FIGS. 17 and 18 to dispense adhesive material therefrom. In a first, fluid adhesive filling one or more of the passageways 188,189, etc. or flexible tubes extending the length of the catheter or its operating head, may be selectively pressurized with a motor or actuator operated by hand to flow such material from the passageways to the cavities coupled thereto for displensing a select quantity or quantities as described. In a second technique, a select quantity of adhesive or adhesive mixture is disposed in the passageway or in each passageway and gas pressure applied behind such material may be applied to cause it to flow into the cavity or cavities in the head or wall of the operating head. In a third technique, small quantities of material(s) to be dispensed are each disposed in a cavity in the end and/or side wall of the catheter or working head, retained therein adhesively or by closure means and caused to be selectively dispensed from the cavity or cavities by gas pressurizing the passageways leading the the cavities, from the other end of the catheter. If the closure or closures extending across the cavity or cavities is made of biodegradeable material which will degrade or dissolve under the effect of body fluid, the material to be deposited may be expelled or allowed to flow freely from the cavities when such biodegradation takes place.

Also shown in FIG. 18 is a send-receive fiber optic bundle 194 extending axially through the catheter and terminating at a wide angle lens 195 for receiving light passed therethrough from a light source at the other end of the catheter, over a wide angle for wide angle viewing of the material immediately adjacent the end of the catheter, such as tissue and body fluid. The wide angle lens 195 is supported in a ferrule secured within a cavity and passageway 193 formed in the end wall 190.

To facilitate retention of the quantities of adhesive material or mixtures of adhesive and the chemical and biological agents described herein against the surface of the tissue on abutted by the walls of the operating heads of the catheters, the cavities 175 and 191 may be coated or lined with a material such as polytetrafluorethylene or the like from which such adhesive material will disengage when the catheter is withdrawn as decsribed.

Various adhesive-drug compositions may be dispensed from the apparatus of FIGS. 1 to 18 as coatings on solid drug units, impregnators of porous implants or dressings or as compositions to be dispensed per se for the purposes of repairing tissue, stopping the flow of fluid such as blood from a wound or slowing releaseing one or more drugs therefrom upon biodegradation within the body. While various adhesives in fluent, tacky state are known in the art which may be utilized per se or in composition or mixture with chemical and/or biological agents selected to perform select functions such as tissue repair, healing, closure, fastening, destruction and/or blood clotting, dissolution of clots or the like, the adhesive formulation used will depend on the application and end results desired by its use. Suitable adhesive substances for many applications are those based upon protiens isolated from marine life, such as the mullusc *Mytilus edulis,* also known as the common Blue Mussel. Ahesives based upon such mussel protein which may be employed by the means described herein and which can be dispensed, as described, in the presence of body fluid to bond to tissue, have been developed by Bio-Polymers, Inc. of Farmington, Conn. and the University of Connecticut Medical School. Accordingly, such bio-adhesives and others may be employed per se or in formulations noted as follows for use with the apparatus described herein:

1. A mixture of a bioadhesive in a tacky fluid condition and a chemical or biological agent or a plurality of either or both such agents laced throughout the adhesive is dispensed per se, as described, against a select area of tissue such as a select portion of the inside wall of a body duct or organ to slowly release such chemical and/or biological agent or agents therefrom per se or as the adhesive biodegrades under the effects of body fluid. Such chemical and/or biological agent(s) may be used to (a) clot blood, (b) prevent blood clotting, (c) destroy cells such as cancer cells of the tissue to which it is attached and/or cells in the body fluid in contact with or distal from the mixture whic is adhered to the select tissue. The adhesive contained agent or agents may also be used to promote or prevent growth of tissue or bone, suppress the secretion of a body fluid or fluids, prevent pregnancy, prevent or detect disease, kill harmful bacteria and/or virus, repair or fasten tissue and bone or perform a combination of two or more of such functions when dispensed as described and bonded to select tissue or bone.

2. A mixture of biodegradeable adhesive and microcapsules may be made of biodegradeable material and containing one or more chemical and/or biological agents for performing one or more of the described types. Various organic and inorganic polymers of the types described in the the article entitled "Improved Drug Delivery" by H. J. Sanders, pp. 31 to 48 of the Apr. 1, 1985 issue of Chemical and Engineering News may be utilized for the microcapsule or matrix material containing the chemical and/or biological agent or agents, it being noted that the bioadhesives also described therein may also be employed for the purposes desribed above. Here again, the density and size of the microcapsules and the agents held thereby will be determined by the end results sought for the particular living being so treated. If the adhesive is body compatible and is slowly biodegradeable under the effects of body fluid to which it is exposed, and the microcapsules or particles of matrix material containing the biological and/or chemical agent or agents, then the biodegradation or surface dissolving of the adhesive after it has set or while in its tacky condition, will progressively expose such particles or microcapsules to the body fluid resulting in the progressive exposure and degradation or dissolution of their walls and time release of their contents.

Variations and improvements in the medical apparatus, compositions and methods for applying and using same described above are noted as follows:

1. Solid materials dispensed by the dispensing means described above and illustrated in such drawings as FIGS. 1 to 4, and 7 to 14 may comprise, in addition to cellular or porous pads, plugs or cylindrical formations of flexible or rigid organic or inorganic polymers impregnated or coated with one or more medications per se, contained in microballoons or microcapsules which are homogeneously mixed in a fluid or fluent material, such as a tacky, biodegradeable self setting or body fluid activated adhesive, formulations of such adhesive-medication mixtures per se which may be dispensed by flowing through an applicator or needle when operated as described herein. Such solid mixtures of medication per se or medication disposed in microcapsules and a binder therefore made of a biodegradeable or dissolvable in body fluid may comprise the dispensed matter described and illustrated in the drawings as being forced by a piston or pivoted fixture through openings in the walls of the catheters, and may be coated, as described with self setting biodegradeable inorganic or bioadhestive material employed to temporarily bond same upon being dispensed, against a select portion of the inside surface of a body duct or internal organ.

2. Where a biodegradeable adhesive is employed as a coating to adhere a biodegradeable pad, plug or otherwise shaped medication or drug containing material or one or more capsules thereof which are biodegradeable to release such drug therefrom, the adhesive is preferably operable to degrade slower than the container or containers of drug or medication bonded therewith, so as to retain the container or containers bonded to tissue while they release their contents to the tissue adjacent thereto, such tissue and/or the volume of the body duct adjacent the tissue.

3. Where the dispensed material is a gauze or bandage material applied against an internal wound to stop internal bleeding and/or supply medication to the wound within the body duct or organ to which it is applied, it may contain a couterizing or blood clotting agent to be applied thereby to the wound or bleeding tissue to or adjacent which the dispensed material is applied.

4. While the dispensing means illustrated in FIGS. 1 to 4 and 7 to 14 have been described as dispensing solid porous medication containing polymers or the like, such dispensing devices may also be employed to position and dispense single containers or capsules which dispense one or more fluid medications through one or more openings to a reservoir or reservoirs within the container and/or from one or more cavities formed in the wall(s) or outer surface(s) of the container after it is disposed, as described, and adhesively bonded to tissue or bone by a bioadhesive by the means described. Such containers may have one or more chambers formed therein containing one or more liquid medications which flow by capillary action through small passageways extending to openings in the wall or walls of the container, either immediately upon disposing and bonding the container in the body or after respective biodegradeable closures or a coating on the surface of the container dissolves or biodegrades and flows into the body to provide openings to the passageways or chambers containing the medication or medications. Cavities and/or passageways extending through the wall or walls of such containers may also contain solid biodegradeable medications or mixtures of medications and biodegradeable solid material to be slowly released therefrom as body fluid penetrates such passageways or cavities and reacts on such solid drug containing material. To effect sustained time release of the same or different medications or drugs from such a container, each medication containing cavity or passageway may be closed off with either a different closure than the others adapted to biodegrade upon exposure to body fluid and release or expose the contents of the passageway to body fluid at a time which is different from the times the other closures biodegrade and expose the contents of their cavities or passageways.

5. The devices of FIGS. 1 to 4 and 7 to 12 may also be employed to dispense and bond containers of instrumentation to select tissue and bone within the body of a living being in the manners described, preferably with adhesive coating or applied thereto to retain such containers in place for a select period of time to be released and expelled from the body when the adhesive biodegrades.

6. While a variety of self setting biodegradeable adhesives may be employed to bond the dressings, medications and described devices to select tissue and bone within the body of a living being, a most suitable adhesive material for many applications is one derived from and based upon a protein isolated from marine biological elements, such as the marine mullusc, *Mytilus edulis* or common Blue Mussel and manufactured by BioPolymers, Inc. of Farmington, Conn., which easily bonds in the presence of water and body fluid. As set forth above, such adhesive may be applied to a surface or surface of the device or material to be adhered to the wall of the body duct or organ in which the catheter is disposed, prior to or during its insertion into the application device or catheter head or as it is moved therethrough or dispensed therefrom. Such adhesive may also be mixed or laced with one or more medications or microcapsules of medication or both and applied, as described, to select areas or internal tissue or injected therein to set and hold the medication or medication containing microcapsules in place until biodegradation results in the release thereof to the body duct and/or tissue adjacent the adhesive.

7. In a modified form of the apparatus of FIGS. 7 to 12 the members 109,109A,121, and 144 may be replaced by an inflatable enclosure, such as a rubber finger or balloon, which is controllably inflated from within the catheter chamber or upon being projected therefrom as described. Such a balloon may contain an adhesive, adhesive mixture or porous flexible material attached to its surface by adhesive or other means and releasable therefrom after being abutted against the surface of the body duct wall by inflation, when the balloon is deflated to permit such material to become applied or adhesively bonded to a select portion of the wall of a body duct. In a particular method employing such application means, the balloon may remain inflated to support the body duct while the adhesive material sets in situ against the body duct wall after which the balloon is deflated and retracted away from the set adhesive or adhesive mixture. Such a balloon may be made of or coated with a material such as polytetrafluoroethylene to permit it to release such adhesive or adhesive coated material or object after the latter is disposed against select tissue, such as body duct wall tissue, adjacent the side wall or front end of the catheter from which the balloon is inflated and expanded outwardly.

8. The apparatus of FIGS. 1 to 4, 7 to 14, 17 and 18 may be employed to apply and adhesively bond living tissue and adhesive compositions containing tissue cells and samples to living tissue, such as wound tissue or specially prepared tissue defining the wall or lining of a body duct such as an artery, digestive canal duct, or duct leading to or extending from a body organ for the purpose of repairing same with new tissue to be grown in situ thereagainst. Such repair tissue samples or cells may be disposed per se or in composition with adhesive material and medication(s) operable to promote the growing together of the applied tissue or cells and the living tissue to which they are so deposited and attached. In the embodiments of FIGS. 1 to 4, the tissue sample or cell containing composition may comprise materials 37 and 37A; in FIG. 7 material 109; in FIG. 8 material 109A; in FIG. 10 material 121 and in FIG. 12 material 144. Cell compositions as described may be disposed in the cavities 175 and 192 of the apparatus of FIGS. 17 and 18 and dispensed therefrom as described to become adhesively bonded to select tissue of the body duct or organ.

Other modifications to the constructions illustrated in the drawings are noted as follows:

1. In the embodiment of FIGS. 1-3 a straight hollow tube or needle, such as a hypodermic needle, may be connected to the piston 36 and urged thereby when the piston is longitudinally moved through the head to penetrate the interface 44 and become projected from the end of the head 32 so as to penetrate tissue or bone immediately adjacent the end of the head and/or expell a fluid through such needle when so projected. Such fluid may be conducted under sufficient pressure applied from the other end of flexible tube 31 and through a passageway formed in the piston 36 when the needle is so projected from the end of the heads 32 or 40.

2. The piston 36 of FIGS. 1-3 may be elongated to permit a portion of the free end thereof to protrude from the end of the heads 32 or 40 while the remaining portion of the piston is supported within the end of the head. Such piston may contain one or more electrodes across which electrical energy may be generated such as direct current or alternating current of predetermined voltage and frequency, which current may be applied through fluid in the body duct and/or directly through tissue or bone which said electrodes are made to contact for beneficially affecting such tissue or bone. For example, such electrical energy may be employed to stimulate the growth of tissue or bone adjacent the bone or tissue contacted by or otherwise electrically coupled to the electrodes of the head. The head or fitting 32 or 40 or a portion thereof may also form one electrode or ground for receiving electrical energy from one or more electrodes insulated therefrom on piston 37 when the latter is projected from the end of the head an electrical energy is passed through a cable or wires extending from an external source through the flexible cable 31, along or through the flexible shaft 30.

3. In a modified form of the embodiment described in 2 above, one or more electrodes operable as described may be supported fixed at the end of the head 31 and protruding therefrom or exposed for contact with a body fluid or tissue against which they are urged or in contact with for electrically energizing same as described. One of such electrodes may be disposed at or near the rear end of the head with the other being located at the front end of the head to permit such current to pass through a substantial portion of tissue adjacent the head when the catheter is properly disposed in a body duct or tissue of a living organism.

4. In the embodiment of FIG. 5 the needle 61 may be electrically connected to a source of electrical energy through a suitable control and energized, as described, when the needle is projected from the head and is penetrating tissue for the purpose of electrically treating such tissue with direct or alternating current. A portion of the head 52 or an electrode disposed thereon and accessible to body fluid or tissue surrounding the head may serve as a ground for electrical energy passing through the tissue from the needle 62.

5. In the embodiment of FIG. 4 the piston 49P may comprise or contain an electrode or electrodes adapted to engage and electrically energize or pass current through tissue such as the wall of a body duct, artery or vein and adjacent tissue when the piston is projected outwardly from the laterall extending bore in which it is movable as described.

6. In all of the embodiments illustrated and described herein, one or more light pipes, such as flexible fiber optical cables or filaments may extend from a viewing means exterior of the catheter at the far end of the flexible tubes 31,70 through or adjacent the described catheter heads or components thereof for providing at a remote location, an image of the tissue or material adjacent the catheter head to permit observation of the tissue to be so operated on or affected as described and/or to provide image information for use or receipt by one or more transducers operable to sense and transduce such information into analyzable electrical signals for diagnostic and control purposes. The light pipe, for example, may extend along the center of or may comprise the flexible shafts 30,66 and may be coupled to a lens or receptor supported by the pistons 36,49P for receiving light directed along one light pipe from a source at the other end of the catheter against tissue adjacent the end of the cathether head or piston and for piping or channelling such light back along the catheter to an external receptor therefore such as view forming optical components or a light-to-electrical energy transducer such as a photodetector.

7. In yet another embodiment of the invention, the heads 32,41,40A and 52 of FIGS. 1-5 and/or the pistons 36,49P may contain embedded therein or wound thereon one or more coils of wire with or without cores and/or other transducers to be energized with electrical energy conducting along the catheter or wires extending along the flexible tube of the catheter when a switch is manually closed or an automatic control operates for inducing electrical current in bone or tissue in the vicinity of such coil when so energized by properly manipulating the catheter to dispose the the head thereof and-/or the piston adjacent selected tissue or bone to be beneficially affected or destroyed by induced electrical energy when the coil is energized, various operations may be performed to the benefit of a light organisms, tissue or bone of a person.

8. A combined coil and electrode arrangement associated with a catheter head or piston as described may be employed wherein both the coil and electrodes may be simultaneously or sequentially energized fro inducing currents in tissue or bone and directly flowing electrical energy through same or different adjacent regions of the human body.

9. In all of the embodiments described above, the flexible tubular portion of the catheter which extends to the operating head may be replaced by a rigid tube or needle support therefore.

10. For those embodiments defined above which employ an electrically energized device such as a motor, solenoid radiation generator or sensor or a plurality of same supported in the operating head of the catheter, the flexible catheter jacket 70 or 70A or a tube flexible tube disposed therein and running the length of the jacket may contain two or more conductors extending along the length thereof and electrically connected at one end to a source of electrical energy and electronic circuitry for processing and analysing signals generated by the transducer and at the head end to the one or more electrical devices mounted in the head. Such conductors may comprise space separated strip-like portions of the extruded plastic tube made of flexible conducting plastic or polymer and strips of an electrically conducting polymer which are cast, printed or extruded along the inside wall of the flexible tube or between layers of extrusion material forming the tube wall. Such conductors may also be in the form of two or more rounded or cylindrical metal wires or flat metal strips which bonded to the inside surface of the jacket or tube comprising the outer wall of the catheter support line 70 or may be embedded in the wall of such tube and attached at their ends to terminal devices such as connectors or directly to the described electrical device and circuit.

11. A flexible light pipe such as an optical fiber or fiber bundle may be similarly attached to or embedded within the side wall of the jacket or a flexible tube within the catheter jacket for conducting light energy to the head or operating end of the catheter for energizing a solar type cell therein adapted receive light conducted by said light pipe thereto for generating electrical energy for energizing one or more electrical devices or electrodes supported by the catherter head and operable to perform treatment and/or diagnostic functions with respect to a living being in which the device is disposed, such as the treatment of a tumor or disease located adjacent the head of the catheter.

12. Any of the catheter operating heads described may contain a lens or other optical device for receiving image defining light which is either generated by a small electrical lamp, directed along a flexible light pipe extending the length of the catheter tube from an external source or generated by a chemical in a reservoir or device inserted in the head and applied to illuminate the tissue or matter immediately adjacent the head in the body or body duct into which the head is inserted wherein such lens is optically coupled to the end of a suitable flexible light pipe extending the length of the catheter tube to a viewing means at the other end of the catheter. Such lens and light pipe-viewer combination may be employed to visually monitor tissue or bone adjacent the head before forcing the small quantity of matter from the head, as described, or before projecting the hollow needle from the head and administering the liquid medication therethrough to tissue.

12. The projectable needle of the embodiments of FIGS. 4 and 6 may contain one or more electrodes or replaced with a device containing one or more electrodes adapted to be disposed thereby when the needle or electrode support is projected, as described, against or into tissue or bone and to apply electrical energy generated and conducted thereto from a source external of the body throug conductors extending the length of the catheter tube or from a battery or cell within the head for the purpose of electrically treating or stimulating such tissue or measuring or detecting and physiological variable with a sensing means defined by or associated with the electrode(s).

13. The embodiments of FIGS. 1–3 and 5 may also be employed to implant a drug releasing capsule or container within a body duct which capsule acts to periodically or upon biodegradation, release a quantity of quantities of medication at the location of such capsule. Such capsule may be bonded or otherwise secured to the tissue against which it is so disposed or allowed to remain or work its way along the body duct until it biodegrades or is otherwise removed.

14. The material released from the catheter heads of the embodiments of FIGS. 1–3 and 5 may comprise miniature containers of a microelectronic circuit, a battery and one or more sensors adapted to be disposed, as described, at a selected location within the body or body duct and to operate thereafter, either continuously or periodically, to sense or detect one or more physiological variables and to transmit data as short wave signals to a receiver outside of the body indicative of such variable(s).

What is claimed is:

1. A method for treating a living being with a medical material delivered to the body of said living being by means of a catheter, said method comprising:
   (a) disposing a select quantity of an encapsulated medical material along with a biodegradeable adhesive in the operating head of a catheter, which catheter includes means for controllably moving said encapsulated medical material and said adhesive from said operating head,
   (b) manipulating said catheter into and through a body duct of the body of said living being to dispose said operating head at a select location in the body of said living being,
   (c) operating said catheter after said operating head has reached said select location to move said encapsulated medical material and said adhesive a distance from said operating head and to dispose said medical material adhesively bonded by said adhesive against a select portion of the surface of said body duct aligned with said operating head,
   (d) removing said catheter from said body duct while leaving said encapsulated medical material adhered to said select portion of said body duct,
   (e) retaining said medical material bonded against the wall of said body duct while allowing said medical material to slowing release from encapsulation and flow to the body of said living being and effect medical treatment within the body of said living being.

2. A method in accordance with claim 1 wherein said medical material is contained within a biodegradeable capsule to which capsule biodegreadeable adhesive is applied and used to effect the adhesive bonding of said medical material to said select portion of said body duct.

3. A method in accordance with claim 1 wherein said medical material is disposed within a plurality of biodegradeable capsules which are retained together as a medical dose and bonded as such to said select portion of said body duct with said biodegradeable adhesive and wherein said biodegradeable capsules are caused to release their contents to the body as they become exposed to and degrade under the effect of body fluid within said body duct.

4. A method in accordance with claim 1 wherein said medical material is adhesively retained within the head of said catheter until it is moved therefrom and adhesively bonded to said select portion of said body duct.

5. A method in accordance with claim 1 wherein the operating head of said catheter has a passageway containing said medical material and an opening at the end of said passageway, said method including urging movement of said medical material and said adhesive through said passageway and out said opening to dispose said medical material against a select portion of the surface of said body duct to adhesively bond same thereto.

6. A method in accordance with claim 1 wherein the operating head of said catheter has a passageway containing said medical material and said biodegradeable adhesive, which passageway extends lateral to the longitudinal axis of said operating head and wherein said operating head has an opening therein at the end of said passageway, said method including urging movement of said medical material through said passageway and out said opening to dispose said medical material against a select portion of the surface of said body duct to adhesively bond same thereto.

7. A method in accordance with claim 1 which includes allowing said adhesive to degrade after said medical material has been released from encapsulation to the body of said living being.

8. A method in accordance with claim 1 which steps (a) to (c) are repeated a number of times to adhesively secure select quantities of said encapsulated medical material against different portions of the wall of said body duct.

9. A method for delivering a medical material of the body of a living being comprising:
   (a) forming a select quantity of medical treatment material,
   (b) disposing a select amount of said medical material in a small container formed with a wall portion thereof made at least partly of a bio-degradeable material which degrades upon contact with body fluid in a manner to release said medical treatment material from said container,
   (c) disposing said small container with a quantity of adhesive secured thereto in the operating head of a dispensing catheter and inserting said catheter into a body duct of a living being,
   (d) working said catheter through said body duct to dispose said operating head in alignment with select body tissue,
   (e) expelling said small container from said operating head to cause it to contact select tissue within the body and to cause said adhesive to bond said container to the tissue it contacts,
   (f) removing said catheter from the body duct,
   (g) allowing body fluid to react on said biodegradeable material of said container while it is adhesively bonded to said tissue in a manner to cause said medical material to become released from said container and to be dispensed therefrom into the body of said living being.

10. A method for delivering a medical material to the body of a living being comprising:
   (a) forming a select quantity of medical treatment material,
   (b) encapsulating said medical material in a plurality of microcapsules formed of bio-degradeable material which degrades upon contact with body fluid in a manner to release said medical material from said microcapsules,
   (c) forming a drug dose defined by a select amount of said microcapsules with an adhesive,
   (d) disposing said drug dose in the operating head of a dispensing catheter,
   (e) inserting said catheter into the body of a living being and disposing the operating head thereof in alignment with select tissue of said living being,
   (f) expelling a select amount of said mixture of microcapsules and adhesive to cause same to contact and become adhesively bonded to said select tissue in the presence of body fluid,
   (g) allowing said body fluid to degrade said microcapsules to permit the medical material contained thereby to be slowly released therefrom.

* * * * *